US010456118B2

(12) United States Patent
McSherry (10) Patent No.: US 10,456,118 B2
(45) Date of Patent: *Oct. 29, 2019

(54) BIOLOGICAL SAMPLE COLLECTION, STORAGE, AND TRANSPORT SYSTEM AND METHOD

(71) Applicant: In HindSight LLC, San Diego, CA (US)

(72) Inventor: Kathleen Mary McSherry, San Diego, CA (US)

(73) Assignee: IN HINDSIGHT LLC, San Diego, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/276,548

(22) Filed: Sep. 26, 2016

(65) Prior Publication Data

US 2017/0071583 A1 Mar. 16, 2017

Related U.S. Application Data

(63) Continuation-in-part of application No. 14/592,589, filed on Jan. 8, 2015, now Pat. No. 9,451,935, which
(Continued)

(51) Int. Cl.
*A61B 10/00* (2006.01)
*A61B 10/02* (2006.01)
(Continued)

(52) U.S. Cl.
CPC ...... *A61B 10/0096* (2013.01); *A61B 10/0045* (2013.01); *A61B 10/02* (2013.01);
(Continued)

(58) Field of Classification Search
CPC . A61B 10/0045; A61B 10/0096; A61B 10/02; C12M 1/30; B01L 2300/046
See application file for complete search history.

(56) References Cited

U.S. PATENT DOCUMENTS 5,129,402 A * 7/1992 Koll ................. A61B 10/0291
600/572
5,477,863 A 12/1995 Grant
(Continued)

FOREIGN PATENT DOCUMENTS

WO 9938996 8/1999
WO 2007009414 1/2007
(Continued)

*Primary Examiner* — Sean P Dougherty
(74) *Attorney, Agent, or Firm* — Sheppard, Mullin, Richter & Hampton LLP (57) ABSTRACT

A biological sample collection, storage, and transport device includes a collection assembly and a sheath, wherein the collection assembly includes a support shaft, a swab head, and a handle, the swab head mechanically couples to a distal support shaft end, the handle couples to a proximal support shaft end, and the collection assembly slideably couples to the sheath and is configurable in a retracted position with the swab head entirely disposed within the sheath or an extended position with the swab head extending outside of the sheath. A distal sheath end includes an aperture, the aperture having a circumference large enough to allow the swab head to pass through said aperture when the collection assembly is configured in the extended position, and a seal is applied to the distal sheath end after the swab head has collected a biological sample and the collection assembly has been reconfigured into the retracted position.

12 Claims, 8 Drawing Sheets

Related U.S. Application Data is a continuation-in-part of application No. 13/301,055, filed on Nov. 21, 2011, now Pat. No. 8,961,896.

(60) Provisional application No. 61/458,407, filed on Nov. 24, 2010.

(51) Int. Cl.

| | | |
|---|---|---|
| *B01L 3/00* | (2006.01) | |
| *C12M 1/30* | (2006.01) | |
| *A61B 90/90* | (2016.01) | |
| *A61B 90/94* | (2016.01) | |
| *C12M 1/00* | (2006.01) | |
| *A61B 34/00* | (2016.01) | |
| *A61B 90/96* | (2016.01) | |

(52) U.S. Cl.
   CPC .............. *A61B 34/25* (2016.02); *A61B 90/90* (2016.02); *A61B 90/94* (2016.02); *A61B 90/96* (2016.02); *B01L 3/50825* (2013.01); *C12M 1/30* (2013.01); *C12M 33/02* (2013.01); *C12M 45/22* (2013.01); *A61B 2010/0061* (2013.01); *A61B 2010/0208* (2013.01); *A61B 2010/0216* (2013.01); *A61B 2034/256* (2016.02); *B01L 2200/0689* (2013.01); *B01L 2300/046* (2013.01); *B01L 2300/069* (2013.01); *B01L 2300/0832* (2013.01)

(56) References Cited

U.S. PATENT DOCUMENTS

| | | | | |
|---|---|---|---|---|
| 5,792,074 | A  * | 8/1998 | Turkel | .......... A61B 10/02 |
| | | | | 600/569 |
| 7,993,871 | B2 | 8/2011 | Skiffington | |
| 8,334,134 | B2 | 12/2012 | Young | |
| 9,451,935 | B2 * | 9/2016 | McSherry | .......... A61B 10/0045 |
| 2002/0012007 | A1 | 1/2002 | Twigg | |
| 2002/0120074 | A1 | 8/2002 | Wada | |
| 2003/0004222 | A1 | 1/2003 | Tanabe | |
| 2003/0012973 | A1 | 1/2003 | Sato | |
| 2003/0042220 | A1 | 3/2003 | Bourreau | |
| 2003/0129738 | A1 | 7/2003 | Sorenson | |
| 2004/0214316 | A1 | 10/2004 | O'Connell | |
| 2007/0255175 | A1 * | 11/2007 | Sangha | ............ A61B 10/0045 |
| | | | | 600/572 |
| 2008/0299600 | A1 | 12/2008 | Bommarito | |
| 2009/0326414 | A1 | 12/2009 | Peltier | |
| 2011/0008869 | A1 | 1/2011 | Bryan | |
| 2011/0087133 | A1 | 4/2011 | Ching | |
| 2011/0088695 | A1 | 4/2011 | Demaria, Jr. | |

FOREIGN PATENT DOCUMENTS

| | | |
|---|---|---|
| WO | 2008030820 | 3/2008 |
| WO | 2010078482 | 7/2010 |

* cited by examiner

BIOLOGICAL SAMPLE COLLECTION, STORAGE, AND TRANSPORT SYSTEM AND METHOD

CROSS-REFERENCE TO RELATED APPLICATIONS

This application is a continuation-in-part of U.S. patent application Ser. No. 14/592,589 filed on Jan. 8, 2015, which claims priority to U.S. patent application Ser. No. 13/301,055 filed on Nov. 21, 2011, the contents of both of which are incorporated herein by reference, and also claims the benefit of and priority to U.S. Provisional Patent Application Ser. No. 61/458,407 filed on Nov. 24, 2010.

TECHNICAL FIELD

The disclosed technology relates generally to collection, storage, and transport of biological samples. More specifically, the present invention relates to systems and methods for collecting, storing, and transporting biological samples, such as cytological cell samples used in anal pap smear procedures.

BACKGROUND

Diagnoses indicating cancer affecting the anus have been on the rise in recent years. Awareness of this medical issue has increased in kind, with many medical professionals encouraging routine screening for early detection.

The anus is the general term for the opening at the lower end of the intestines, but can informally refer to both the anal opening and the anal canal. The anal canal spans from the rectum to the anal verge, where the canal meets the outer skin of the anus. There are a number of different cell types that make up the rectum, anal canal, and anus. The upper anal canal and some of the nearby rectal tissue comprises tiny column-like cells. Cells near the mid-section of the anal canal are cube-shaped transitional cells. Flat squamous cells comprise the lower anal canal, anal verge, and the perianal skin. Most anal cancers in the United States are squamous cell carcinomas, but anal cancer can also take the form of adenocarcinomas that develop in the cells that line the upper part of the anal canal near the rectum, or in glands located under the inner lining of the anal canal. The presence of anal cancer can show a variety of symptoms including anal bloat, lumps, rectal bleeding, itching, or discharge.

A significant number of anal cancers derive from human papillomavirus (HPV) infections, a sexually transmitted disease. HPV also causes anogenital warts, which can cause anal carcinomas to form. Individuals with a history of anal warts are known to be at risk of developing anal cancer. HPV has also been shown to be a leading cause in cervical cancer in women, and, as such, methods of detection of anal cancer can be seen as counterparts to cervical methods. One such method of detecting cervical cancer is the cervical Pap smear, in which cells are collected from the cervix for analysis to detect cancerous characteristics. Currently, similar methods can be used for cells collected from the rectoanal region to detect anal cancer.

In a typical anal Pap smear procedure, a collection instrument, such as a small brush or a cotton-tipped or DACRON® swab, is inserted into the orifice. The brush or swab is swiped along the surfaces of the orifice tissue to collect a sample of the cells. These collected cells may be suspended in a liquid transport medium after collection, such as a suitable collection and storage fluid used for medical samples. In either case, the collected cells are examined for characteristics indicating cancerous cell growth, generally done by a trained pathologist. In some instances, mechanized examination of the cell samples has automated the initial screening to flag candidates for closer examination. The cell samples may be smeared on a glass slide or remain in suspension for the examination process. The examination process may be by use of imaging, two-sided immunoassay, or any other method of cellular sample examination.

The cell collection portion of a Pap smear procedure can be performed in a doctor's office. However, the procedure itself does not require significant invasive techniques. Thus, the need to visit a doctor specifically for such a procedure is not inherently required, so long as the collection of cells can be done in such a way that the cells are properly collected, preserved, and transported to a pathologist intact for analysis.

While devices relating to cervical Pap smears have been developed and may be applicable to the detection of anal cancer, these kits do not take into account the differences in the structural anatomy between the cervix and the anus/anal canal. One embodiment of the present invention addresses this need by a device specifically for the collection and preservation of cytological cell samples taken from the anus and anal canal.

BRIEF SUMMARY OF EMBODIMENTS

In certain aspects, a device for collecting, storing, and transporting cells for cytological analysis is provided. In one embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slideably coupled through the base at the support shaft such that at a first slide position the swab head is located within the sheath and the plunger is located external and distal to the base, and at a second slide position the swab head is displaced through the opening at the head end of the sheath; wherein the base and containment vial are configured to engage with each other to form a seal and enclose the sheath and collection assembly within an internal volume defined by the containment vial and base; and wherein the plunger comprises a lock that locks the plunger in the base when the collection assembly is in the second slide position. The lock optionally comprises a click lock that produces an audible "click" when the collection assembly is locked in the second slide position. The plunger is optionally engaged with the base when the collection assembly is in the second slide position.

In some embodiments, the collection assembly may be retracted back into the sheath once a biological sample has been collected and the sheath may be sealed. For example, the seal may be an adhesive seal configured to cover the distal opening of the sheath, or the seal may be a cap configured to mechanically couple to the distal end of the sheath.

In other embodiments, the plunger may frictionally couple within the base when the plunger is engaged in the second position. For example, a radially outward facing surface of the plunger may contact and apply a normal force to a radially inward facing surface of the base. The materials selected to form the base and the plunger may be selected to have sufficiently high coefficients of static friction such that, when the normal force is applied as described above, the plunger is secured in a static position within the base such that standard contact, dropping, or moving of the collection assembly will not dislodge the plunger from the base.

In another embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slideably coupled through the base at the support shaft such that at a first slide position the swab head is located within the sheath and the plunger is located external and distal to the base, and at a second slide position the swab head is displaced through the opening at the head end of the sheath; wherein the base and containment vial are configured to engage with each other to form a seal and enclose the sheath and collection assembly within an internal volume defined by the containment vial and base; and wherein the plunger comprises a lock that locks the plunger in the base when the collection assembly is in the second slide position. The plunger is optionally engaged with the base when the collection assembly is in the second slide position. The lock optionally comprises a click lock that produces an audible "click" when the collection assembly is locked in the second slide position. The base optionally comprises a receiving channel to receive the plunger and engage the click lock when the collection assembly is in the second slide position. The base also optionally comprises a mating structure configured to engage with the lock.

In yet another embodiment, the device comprises a collection assembly comprising a swab head and support shaft; a plunger connected to the support shaft opposite the swab head; a sheath having a head end and a foot end, configured to enclose at least the swab head and support shaft within its internal volume, and comprising an opening at the head end configured to pass the swab head; a base connected to the foot end of the sheath; and a containment vial; wherein the collection assembly is slideably coupled through the base at the support shaft such that at a first slide position the swab head is located within the sheath and the plunger is located external and distal to the base, and at a second slide position the swab head is displaced through the opening at the head end of the sheath and the plunger is engaged with the base; wherein the containment vial is configured to engage with a cap to form a seal and enclose the sheath and collection assembly within an internal volume defined by the containment vial and cap; and wherein the plunger comprises a lock that locks the plunger in the base when the collection assembly is in the second slide position. The support shaft optionally comprises a support stop that engages with the interior surface of the head end of the sheath when the swab is in the second slide position. Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The following description is not to be taken in a limiting sense, but is made merely for the purpose of describing the general principles of the disclosed embodiments. The present embodiments address the problems described in the background while also addressing other additional problems as will be seen from the following detailed description. Numerous specific details are set forth to provide a full understanding of various aspects of the subject disclosure. It will be apparent, however, to one ordinarily skilled in the art that various aspects of the subject disclosure may be practiced without some of these specific details. In other instances, well-known structures and techniques have not been shown in detail to avoid unnecessarily obscuring the subject disclosure.

Some embodiments of the disclosure provide a system for biological sample collection. As disclosed herein, a system for biological sample collection may include a collection assembly and a sheath. The collection assembly may include a support shaft, a swab head, and a handle. For example, the swab head may be flocked fiber, cotton, plastic, or other fabric designed to accept a transfer of biological material (i.e., cells, fluids, DNA, or other biological material) when the swab head comes in contact with a collection site. The handle may be a plunger, a ring, or other shapes as known in the art. For example, if the handle is a ring, the ring may be shaped to fit a finger or a thumb as to enable one-handed operation of the device.

In some embodiments, the swab head mechanically couples to a distal support shaft end and the handle couples to a proximal support shaft end. The collection assembly may slideably couple to the sheath. For example, the collection assembly may be configurable in a retracted position with the swab head entirely disposed within the sheath or an extended position with the swab head extending outside of the sheath, or other intermediate positions therebetween.

In some examples, the distal sheath end may include an aperture with a circumference large enough to allow the swab head to pass through said aperture. In some examples, the aperture may be covered by a seal to create a sterile environment inside of the sheath when the system is not in use (e.g., during transportation or storage). The seal may then be broken by the swab head when the collection assembly is placed into the extended position.

In some embodiments, the system may also include an attachable seal that may be applied to the distal sheath end after sample collection. For example, the collection assembly may be retracted back into the retracted position once the sample is collected and the second seal may be applied to the distal sheath end, enclosing the swab head and the biological sample within the sheath. The attachable seal may include an adhesive backing to enable adhesion to the distal sheath end (or alternatively, the distal sheath end itself may include the adhesive coating). In other embodiments, the system may include a cap configured to fit over the swab head and create a seal with the distal sheath end when the collection assembly is in the retracted or extended position.

In some examples, the sheath may be configured to fit into a palm of a hand and the handle comprises a ring configured to fit around a finger or thumb from the hand to enable one-handed operation of the collection assembly into the retracted position or the extended position.

In some examples, the handle may be larger than a circumferential profile of a proximal sheath end and the handle contacts the proximal sheath end when the collection assembly is in the extended position, as to prevent the collection assembly from being over-extended.

Some embodiments disclose a method for biological sample collection. The method may include identifying a collection site. For example, the collection site may be a nasal cavity, an oral cavity, a vaginal cavity, an anal cavity, or any other biological sample collection site of interest. A collection device, consistent with the collection devices disclosed herein, may be used to collect the biological sample. For example, the method may include configuring the collection device in a first position, such that the swab head is completely disposed within the sheath and the handle extends proximally from a proximal sheath end. The method may also include moving a distal end of the sheath close to the collection site and reconfiguring the sample collection device into a second position by applying pressure to the handle, such that the swab head fully extends through a distal opening in the sheath and the handle contacts a proximal end of the sheath, and applying the swab head to the collection site to collect a biological sample.

In some examples, the method may include placing a cap over the swab head and sealably coupling the cap to the distal sheath end, when the collection assembly is in the retracted or extended position. In other examples, retracting the collection device into the first position and resealing the sheath by adhering a seal to the opening in the distal end of the sheath, thereby sealing the swab head and biological sample therein.

In other embodiments of the disclosure, a method for biological sample collection may include identifying a collection site and providing a biological sample collection device according to embodiments disclosed herein. The method for biological sample collection may further include configuring the collection device in a first position, such that a swab head of a collection assembly is completely disposed within a sheath of the biological sample collection device, and a plunger of a collection assembly extends proximally from the base of the biological sample collection device. The method may further include moving a distal end of the sheath close to the collection site and reconfiguring the sample collection device into a second position by applying pressure to the top surface of the plunger, such that the swab head fully extends through a proximal opening in the sheath to contact the collection site and the plunger interfaces with the stop. The method may further include removing the swab head from the collection site.

According to some embodiments, the method for biological sample collection may be performed using one hand. For example, the sheath may be held in one hand and the plunger may be depressed using a thumb. Accordingly, the method may be self-administered. In some embodiments, the method may further include frictionally coupling the plunger within the base when the collection device is in the second position. The method may further include engaging the used collection device in a vial and sealing the vial to the base to contain the biological sample.

In some embodiments, a system for biological sample collection also includes a biological sample identification server and a mobile device. The mobile device may be a smart phone, a laptop, a tablet computer, or other mobile device as known in the art. The mobile device may include a processor and non-volatile computer readable memory with software embedded thereon, the software configured to receive a request to collect a biological sample from the biological sample identification server. For example, the request may include specific collection instructions and patient demographic information transmitted in an encrypted format. The software may then cause a display on the mobile device to display instructions to a user related to the request. The software may receive an identification data set from a sensor coupled to the mobile device. For example, the sensor may be a bar code reader, an RFID reader, a QR reader, or other type of sensor configured to detect and uniquely identify a biological sample as known in the art. The software may further be configured to accept a user input indicating when sample collection has been completed. In some examples, the software may cause a printer to print a label to attach to the biological sample device to uniquely identify the sample. The software may also cause a printer to print a shipping label to send the sample back to a laboratory.

Figure 1:
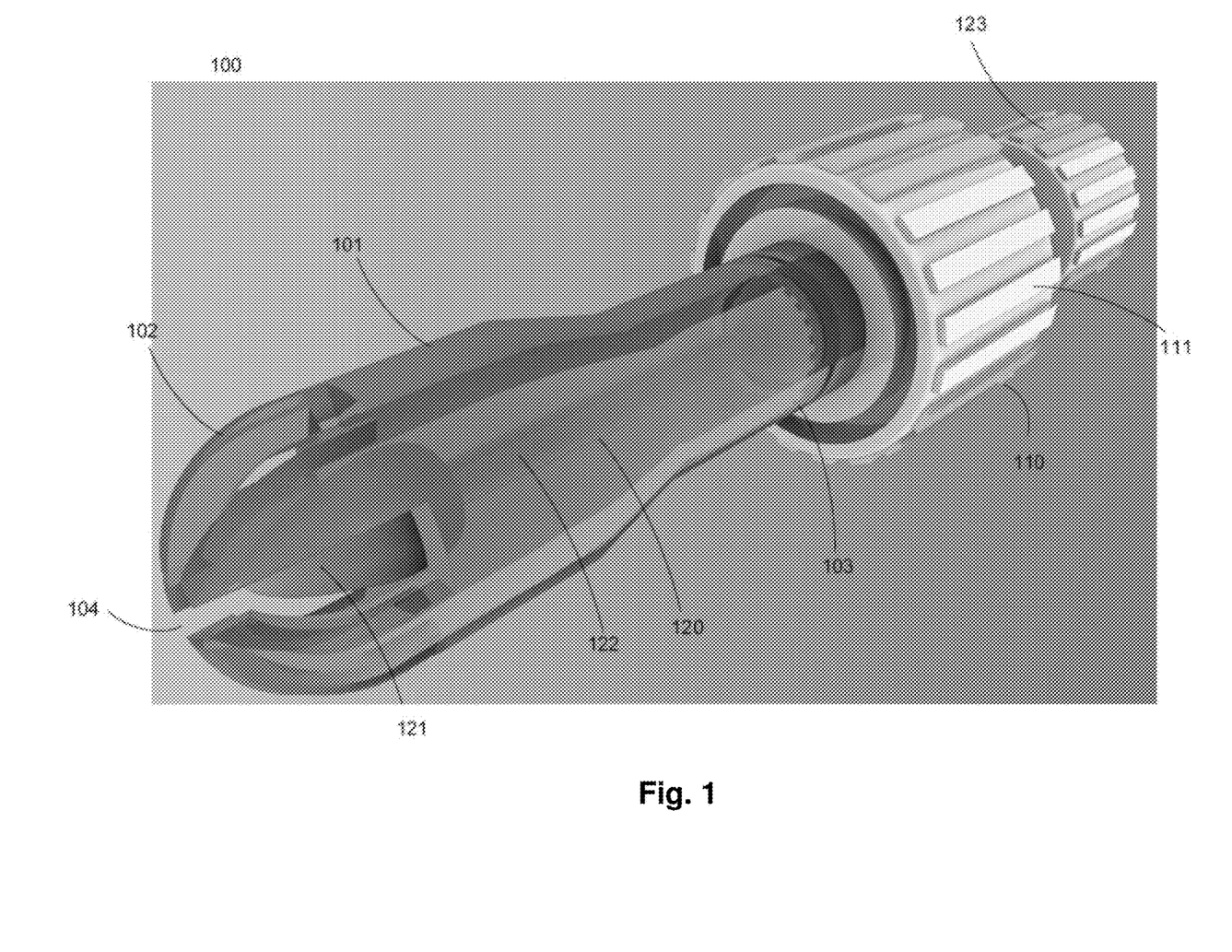
FIG. 1 is a diagram of a component of a cell collection, storage, and transport device in a first slide position according to one embodiment.

FIG. 1 shows an example embodiment of a component 100 of a device for cell collection, storage, and transport. The device in this example comprises sheath 101 having a head end 102 and foot end 103, connected to a base 110 at the foot end 103. The device also comprises a collection assembly 120, which further comprises a swab head 121 and a support shaft 122. A plunger 123 is connected to the support shaft 122 opposite the swab head 121 and is located exterior of the base 110. An opening 104 on the head end 102 is configured to pass the swab head 121. The collection assembly 120 is slideably coupled through the base 110 and at the support shaft 122, allowing the collection assembly 120 to be placed at a first or second slide position. As illustrated in FIG. 1, the device is shown with the collection assembly 120 in the first slide position, wherein the swab head 121 is located within the sheath 101, and the plunger 123 is located some distance distal and external to the base 110.

The swab head, which is the collection surface of the device, can be formed of any variety of materials that effectuate proper cell collection. Examples of such materials include, without limitation, cotton, Dacron®, foam fiber, brush fibers, and flocked fibers. The swab head shape may also be formed into suitable shapes based on the anatomy of the tissues targeted for collection. Examples of such shapes include, without limitation, bulbous, triangular, conical, brush, and cylindrical.

In the example embodiment of FIG. 1, the head end 102 of the sheath 101 is bulbous, with the opening 104 comprising a 4-petal structure. The bulbous head in this embodiment provides comfort to users of the device during the initial insertion of the device into the body cavity. Gentle pressure of the bulbous head end 102 against the entrance of the user's body cavity aids in comfortably widening the entrance to the cavity, thus allowing for proper extension of the collection assembly 120 into the interior of the body cavity for effective cell collection. The shape of the head end 102 and opening 104 can take other forms based on the body cavity or anatomy targeted for cell collection.

The lateral surface of the base 110 in FIG. 1 is illustrated with ribs 111, which aid users of the device in gripping the base during rotation of the device in the cell collection procedure. The base 110 may optionally be textured, formed in a specific shape, or comprise a grip-enhancing material to provide a user with adequate control during the cell collection procedure.

Figure 2:
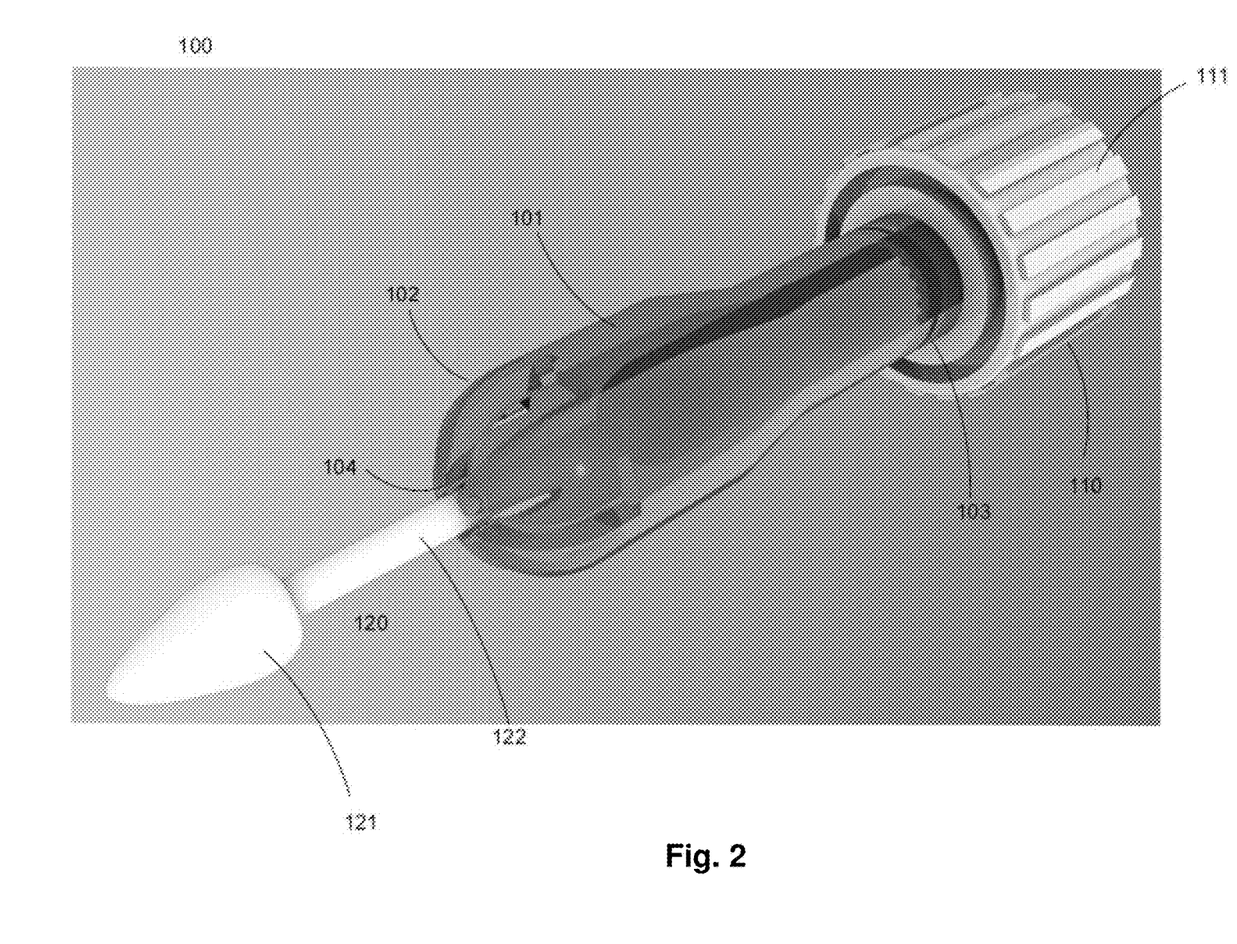
FIG. 2 is a diagram of a component of a collection, storage, and transport device in a second slide position according to one embodiment.

FIG. 2 shows the component 100 of FIG. 1 in the second slide position. When the collection assembly 120 is in the first slide position of FIG. 1, a user of the device that wishes to collect a cell sample slides the collection assembly 120 into the second slide position by pushing the plunger 123 toward the base 110. The sliding of the collection assembly 120 into the second slide position displaces the swab head 121 though the opening 104 for exposure to tissues targeted for cell collection. As can be seen in FIG. 2, when plunger 123 is pushed, the swab head 121 is extended at the exterior of the sheath 101 and is exposed for cell collection when the device is in the second slide position.

Figure 3A:
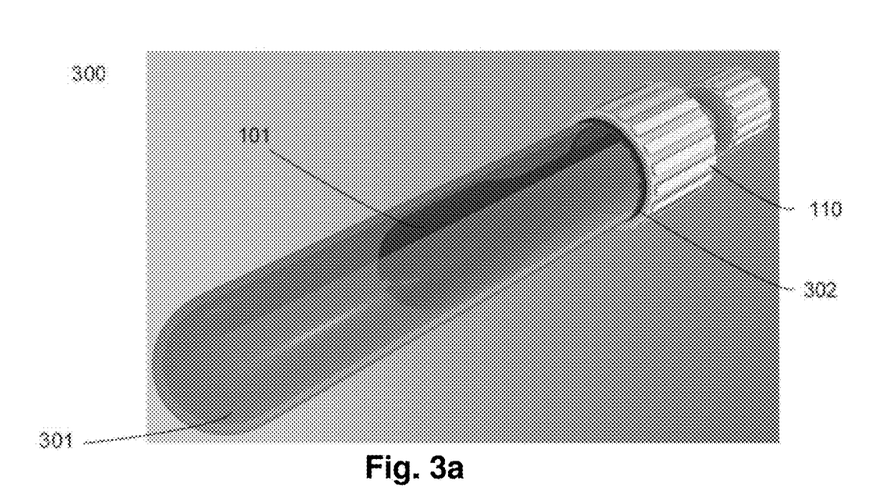
FIG. 3A is a diagram of a cell collection, storage, and transport device in a first slide position according to one embodiment.

Generally, the collected cells must be transported to a laboratory for examination and analysis. In various embodiments, the component 100 may be combined with a suitable container configured to engage with the component 100 to make the collection, storage, and transportation of the collected samples easier. FIG. 3A shows an example embodiment of a device 300 for cell collection, storage, and transport. This example incorporates the component 100 of FIG. 1 (i.e., the component 100 of the device in the first slide position) enclosed by a containment vial 301. The containment vial 301 is configured to engage with and form a seal 302 with base 110 to sealably enclose the sheath 101 and collection assembly 120. As can be seen, the sheath 101 and the collection assembly 120 in the first slide position is enclosed within the volume defined by the containment vial 301 and base 110. Receiving the device in this configuration as part of an at-home kit, for example, would indicate to potential users that the device is in a "ready to use" state.

Figure 3B:
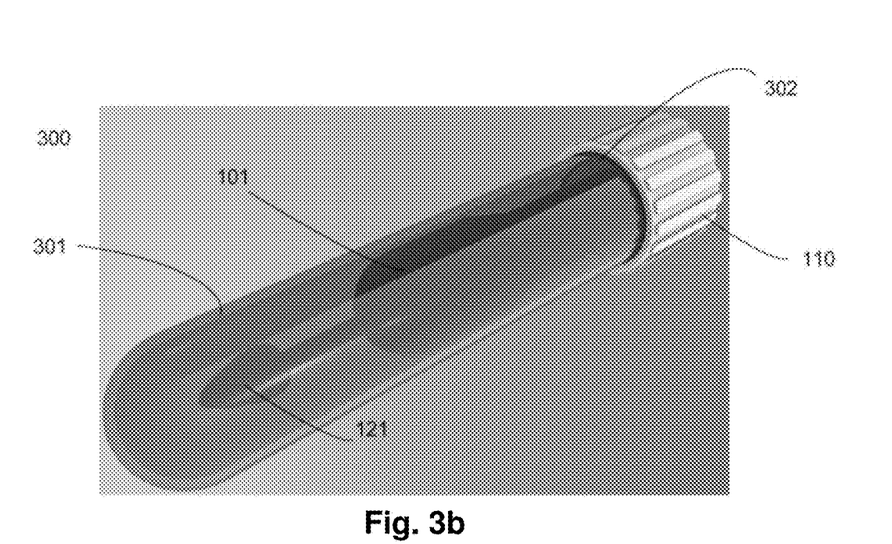
FIG. 3B is a diagram of a cell collection, storage, and transport device in a second slide position according to one embodiment.

FIG. 3B shows an example embodiment of a device 300 for cell collection, storage, and transport incorporating the component 100 of FIG. 2 (i.e., the component 100 of the device in the second slide position) also enclosed by the containment vial 301. As can be seen, the swab head 121 has been passed through the opening and is located external to the sheath 101 in the second slide position. The sheath 101 and collection assembly 120 are enclosed within the internal volume defined by the containment vial 301 and base 110. The device in the second slide position can indicate to potential users that the device has been used and is ready for transport to a testing facility. FIGS. 3A and 3B illustrate that the containment vial 301 is dimensioned such that the containment vial 301 and base 110 enclose the collection assembly 120 and sheath 101 within the internal volume defined by the containment vial 301 and base 110 when the collection assembly 120 is in either the first slide position or the second slide position configurations.

The containment vial 301 can be configured to engage with the base 110 in a number of ways that provide a seal. Examples of such configurations include, without limitation, mating screw threads, pressure-fit locking threads or tabs, or other mechanisms. Sealing grommets, rings, or linings can be used to enhance the sealing capabilities of the interface between the containment vial 301 and base 110. In various embodiments, the containment vial 301 may include an area on the containment vial's external surface for recording identifying information for the sample. Such information could include, but is not limited to, one or more of: the name of the subject from which the collection was taken, the date of collection, and the site from which the sample was taken, or any combination thereof.

Although the containment vial 301 is discussed above as being configured to engage with the component 100, this description should not be read to limit the present disclosure. In various embodiments, containment vial may be configured to encapsulate the component 100 entirely and include a separate sealing cap for use in sealing the containment vial.

Locking mechanisms can be provided on plunger 123 to releasably lock the plunger 123 in place within base 110 such as for transport or storage. Although specific locking mechanisms are not illustrated, one of ordinary skill in the art after reading this description will understand that any of a number of different locking mechanisms can be used to secure plunger 123 in base 110 such as, for example, threads, tabs, friction fit and so on.

Figure 4A:
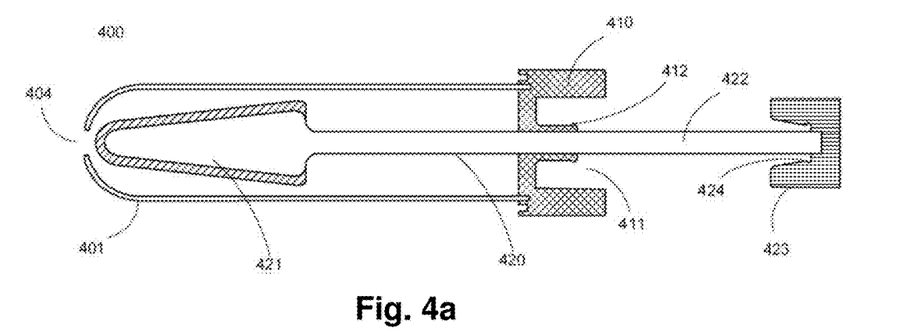
FIG. 4A is a diagram showing the cross section of a component of a cell collection, storage, and transport device in a first slide position according to one embodiment.
Figure 4B:
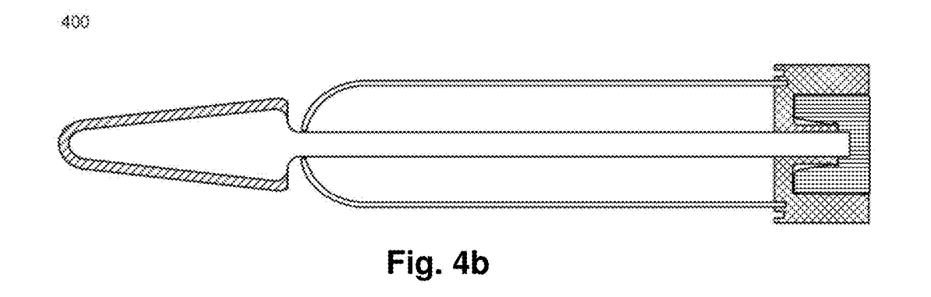
FIG. 4B is a diagram showing the cross section of a component of a cell collection, storage, and transport device in a second slide position according to one embodiment.

FIGS. 4A and 4B show a cross-sectional view of a component 400 of another embodiment of a device for cell collection, storage, and transport. A collection assembly 420, comprising a swab head 421 and support shaft 422, is located within a sheath 401 and is slideably coupled through a base 410. The collection assembly as shown in FIG. 4A is in a first slide position, and the plunger 423 is external and distal to the base 410. A user of the device slides the plunger 423 toward the base 410 to put the collection assembly into the second slide position, thereby extending the swab head 421 through the opening 404. The base 410 is configured to receive the plunger 423 when in the second slide position via a receiving channel 411. The plunger 423 comprises a lock 424 that engages with the base 410 while in the receiving channel 411. The lock 424 restricts the user from retracting the collection assembly 420 back into the sheath 401 (i.e., return the collection assembly 420 to the first slide position). Other benefits to the locking facility of the lock 424 include assuring the user that the collection assembly 420 is firmly seated in the base 410 to allow for effective collection of cells from the target tissue, providing resistance to opposing pressure during sampling, and preventing overextension of the collection assembly 420 into the user's body cavity. Incomplete extension and premature or unintended retraction of the collection assembly 420 into the sheath 401 can lead to inconsistent or faulty cell collections which would adversely affect proper cell analysis. Additionally, potential users can avoid devices found locked in the second slide position, which may indicate that the device had already been used.

The lock 424 optionally comprises a click lock, preferably configured to provide an audible "click" sound when engaged with the base 410, which signifies to the user that the collection assembly 420 is fully extended and ready for proper cell collection. In the example embodiment of FIGS. 4A and 4B, the lock 424 is formed by a raised lip on the plunger 423, which is dimensioned for a pressure-fit with a mating structure 412 in the receiving channel 411 on the base 410. The audible click is generated as the raised lip passes into the receiving channel 411 and over the mating structure 412 on base 410.

The lock is not limited to location with respect to the base and the sheath, as the lock may optionally be located within the sheath when the collection assembly is in the second slide position. Further, the lock may optionally engage the sheath to provide the locking functionality.

As can be seen in FIG. 4B, the plunger 423 is formed to be flush with the shape of the receiving channel and with the outer surface of the base when in the second slide position. In one embodiment, the device comprises a circular base that is configured with a circular receiving channel at a specified depth. The plunger is configured with a complementary circular form that sits flush with the sides of the receiving channel when the collection assembly is in the second slide position, and with a specified thickness matching that of the depth of receiving channel such that the plunger is also flush with the outer surface of the base.

The plunger 423 can also be formed into any number of shapes based on the intended methods for collecting or the anatomy of the tissues targeted for cell collection. For example, a ball-type plunger may be contemplated to aid in the rotation of the device during the collection stage.

The receiving channel 411 and lock 424 may be configured to be sealably engaged to resist leakage of fluid, if suitable collection and storage fluid is used. Mechanisms to form such seals, while retaining the "click" functionality, include mating screw threads on both the plunger 423 or base 410, or locking tabs, and may be combined with sealing grommets or linings to enhance the fluid seal.

In the embodiment illustrated in both FIGS. 4A and 4B, the containment vial (not shown) engages with and forms a seal with the base 410 to enclose the sheath 401 and collection assembly 420 when the collection assembly 420 is in either the first slide position or the second slide position.

In an example of using the device in an at-home anal cytological cell collection procedure, a user receives the device with the sheath and collection assembly enclosed the containment vial, with the collection assembly in the first slide position. The user first removes the containment vial to expose the sheath. The opening on the sheath is pressed against the anal entrance. Pressing the bulbous head end of the sheath against the anal entrance provides greater comfort to the user in guiding the swab head into the anal canal, as the insertion of the sheath helps to widen the anal entrance and resists the outward pressure from the muscles in the external anal sphincter. The plunger is then displaced to move the collection assembly from the first slide position into the second slide position and locked via the click lock into the second slide position. The user, hearing the click of the click lock, is then assured that the swab head is properly extended and exposed to the rectal tissue for collection. With the device still firmly inserted and in the second slide position, the user rotates the device to effectuate cell collection. To ensure proper collection, the user optionally rotates the device both clockwise and counterclockwise multiple times. In a non-limiting example, the user may optionally rotate the device five times clockwise and five times counterclockwise. Afterwards, the user gently removes the device from the anus, places the containment vial over the sheath and collection assembly and engages the collection vial with the base to seal it. The entire device can then be transported to a facility for analysis.

According to aspects within the present disclosure, the device can be used for dry collection of cells at targeted tissues. However, wet collection and containment may also be implemented using the device. For instance, the swab head may be pre-moistened with a suitable cell collection fluid, or the containment vial may be pre-filled with fluid suitable to suspend or store collected cells for transport. Additionally, suitable collection, suspension, or storage fluid may be provided for the user to apply.

Figure 5:
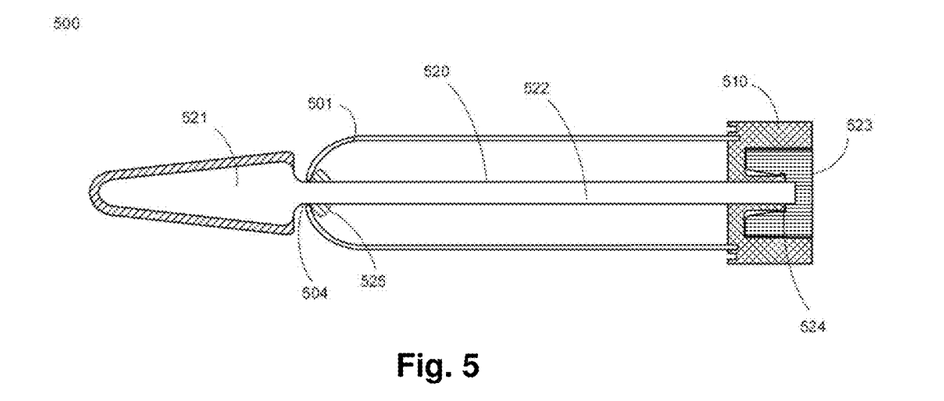
FIG. 5 is a diagram showing the cross section of a component of a cell collection, storage, and transport device in a second slide position according to one embodiment.

FIG. 5 illustrates another embodiment of a component 500 of a device for cell collection, storage, and transport according to aspects of the present disclosure. The component 500 comprises a collection assembly 520 comprising a swab head 521 and support shaft 522; a plunger 523 connected to the support shaft 522 opposite the swab head 521; a sheath 501 having a head end and a foot end, configured to enclose at least the swab head 521 and support shaft 522 within its internal volume, and comprising an opening 504 at the head end configured to pass the swab head 521; a base 510 connected to the foot end of the sheath 501; and a containment vial (not shown); wherein the collection assembly 520 is slideably coupled through the base 510 at the support shaft such that at a first slide position the swab 521 head is located within the sheath 501 and the plunger 523 is located external and distal to the base 510, and at a second slide position the swab head 521 is displaced through the opening 504 at the head end of the sheath 501 and the plunger 523 is engaged with the base 510; wherein the base 510 and containment vial (not shown) are configured to engage with each other to form a seal and enclose the sheath 501 and collection assembly 520 within an internal volume defined by the containment vial (not shown) and base 510; and wherein the plunger 523 comprises a lock 524 that locks the plunger 523 in the base 510 when the collection assembly 520 is in the second slide position. The component 500 in FIG. 5 is shown in the second slide position. The support shaft 522 optionally comprises a support stop 525 that engages with the interior surface of the head end of the sheath 501 when the swab 521 is in the second slide position.

The device, while applicable to at-home cell collection procedures, may be used by medical professionals in hospitals and clinics as it offers a convenient configuration for cell collection, containment, and transport.

In some embodiments, the plunger may be secured within the base using frictional coupling. Frictional coupling is created when a radially outward surface of plunger 123 contacts a radially inward surface of base 110, creating a resistive force that restricts the movement of plunger 123 relative to base 110.

Figure 6:
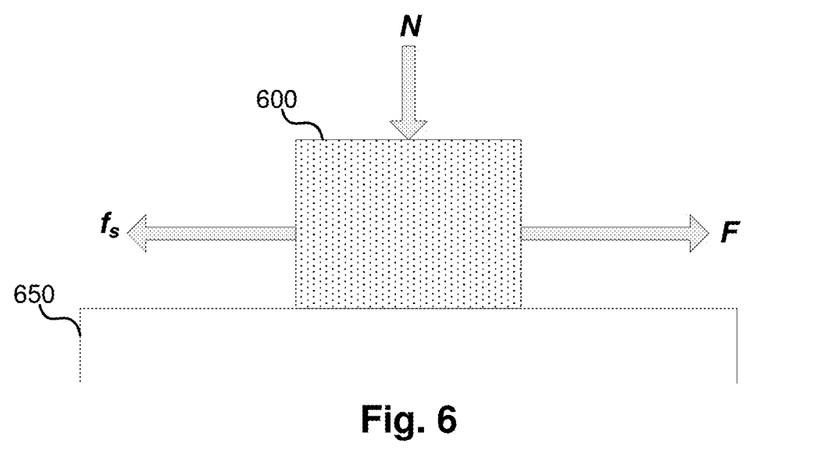
FIG. 6 is a diagram illustrating frictional resistance as applicable to some embodiments disclosed herein.

FIG. 6 is a diagram illustrating frictional resistance. As illustrated, when a normal force N is applied to object 600, the direction of force N being orthogonal to surface 650, at the same time that force F is applied to object 600 in a direction that is parallel to surface 650, frictional force $f_s$ is created, in an opposing direction to force F.

Still referring to FIG. 6, when an object moves over the surface of another object, movement is generally opposed by a counteracting resistive frictional force. A coefficient of friction may be defined as a scalar value that represents the relationship between the frictional force and the normal force applied between the two objects. The coefficient of friction may be represented as $\mu = f/N$, where f is the force of friction and N is the normal force. The coefficient of friction is a property of a particular material or materials that come into contact with each other. Generally, the coefficient of friction describes the propensity of either material to resist lateral motion when two objects composed of those materials come into contact with each other. The range of the coefficient of friction is generally bound between 0 and 1, where a value of 0 indicates the absence of friction between two objects and the value of 1 indicates the presence of frictional force equal to the normal force. For example, the resulting coefficient of friction for ice contacting ice is very low—approximately 0.02-0.09. In contrast, the resulting coefficient of friction for rubber contacting asphalt is very high—approximately 0.9.

Typically, materials have two different coefficients of friction. The first coefficient of friction is known as the coefficient of kinetic friction, and describes the relative resistance between two materials that are already moving laterally with respect to each other. The other coefficient of friction is the coefficient of static friction, which describes the relative resistance between two materials that are in contact, but not moving. Typically, the coefficient of static friction is higher than the coefficient of kinetic friction, meaning that it is harder to make an object start to move then it is to keep the object moving. Thus, static friction describes the frictional force between two surfaces that attempt to slide one object across the other, but result in no movement with respect to each other. As a result, the friction is always equal to the net force parallel to the surface, described as, $f_s^{max} = \mu_s N$, where $f_s^{max}$ is the static frictional force and $\mu_s$ is the coefficient of static friction. In order to calculate the force required to overcome normal force and enable movement of an object, the following equation is calculated:

$$\sum F_y = N - \text{mg} - F\sin\theta = 0 \qquad (1)$$

$$N = \text{mg} + F\sin\theta \qquad (2)$$

$$\sum F_y = F\cos\theta - F_s > 0 \qquad (3)$$

$$F\cos\theta - \mu_s > 0 \qquad (4)$$

$$F\cos\theta - \mu_s(\text{mg} + F\sin\theta) > 0 \qquad (5)$$

$$F\cos\theta - \mu_s F\sin\theta > \mu_s \text{mg} \qquad (6)$$

$$F > \frac{\mu_s \text{mg}}{\cos\theta - \mu_s \sin\theta} \qquad (7)$$

Accordingly, as applied to the embodiments of the current disclosure, when force F is applied to the outward facing radial surface of the plunger at angle θ (for example, θ may equal $$\left(\frac{\pi}{2}\right))$$

with mass m and a coefficient friction of $\mu_s$, cos θ is equal to $\mu_s$ sin θ, which prohibits the plunger from moving or rotating. However, when force F is greater than the static friction $F_s$, the plunger is free to move and rotate within the base since there is lack of frictional force to ensure that the plunger stays in the second slide position through frictional resistance.

Figure 7:
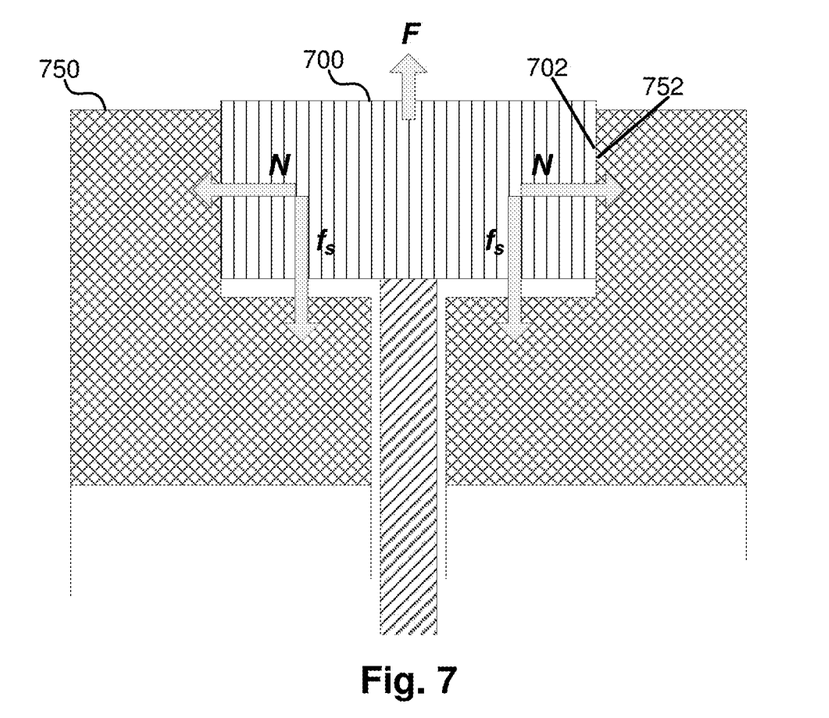
FIG. 7 is a diagram showing a cross section of a plunger disposed inside a base of a cell collection, storage, and transport device according to some embodiments disclosed herein.

FIG. 7 is a diagram showing a cross-section of a plunger disposed inside a base of a cell collection, storage, and transport device. Referring to FIG. 7, plunger 700 may frictionally couple to base 750 when plunger 700 is disposed within base 750. As illustrated, radially outward facing plunger surface 702 may contact radially inward facing base surface 752 when plunger 700 is disposed within base 750. Moreover, the diameter of base 700 may be designed to be approximately the same size as, or even just slightly larger than the inside diameter of base 750 such that radially outward facing plunger surface 702 may press against radially inward base surface 752 and generate normal force N. Accordingly, frictional coupling occurs when the coefficient of static friction between the respective materials that comprise base 750 and plunger 700 is sufficiently high such that $f_s$ equals or exceeds an outward force F (e.g, outward force F may be the weight of the sheath, collection swab head, and plunger when the collection assembly is held with the plunger facing downward relative to the collection assembly distal end 501, such that the plunger is held in place by frictional force $f_s$).

In some embodiments, plunger 700 and base 750 comprise materials with a relative coefficient of friction of between 0.06-0.85, enabling the plunger to stay in the second slide position through frictional resistance. In some examples, plastics with coefficients of friction of between 0.10 and 0.50 may be selected. For example, polytetrafluoroethylene (PTFE) may be selected with a coefficient of friction of between 0.10 and 0.30. In other examples, polyethylene may be selected with a coefficient of friction of between 0.15 and 0.25. In other examples, nylon may be selected with a coefficient of friction of between 0.30 and 0.60, allowing the plunger to stay fitted within the walls of the base and create an effective seal. Other materials may be selected based on their relative properties, including melting points, resilience, compression strength, hardness, density, propensity for sterilization, coefficient of friction, and cost.

Given the relative weight of most plastics, even plastics with low coefficients of friction (in the range of 0.06 to 0.40) may be selected so long as the material also has a sufficient resilience and compression strength so that the plunger can be formed with an outer diameter just exceeding the inside diameter of the base, such that the plunger may be slightly compressed to enable it to fit within the base, but then will expand outward again generating normal force N to be at least $$\frac{F}{\mu}$$

where F equals the combined weight of the plunger, sheath, collection swab head, and collected sample and μ equals the coefficient of friction of the material, as described above. Accordingly, a wide range of materials with different coefficient of frictions may be selected, so long as the above described relationships are maintained involving the relative weight of the sheath, plunger, and swab head, and the resilience, compressive strength, relative diameters, and coefficient of friction of the materials comprising the base and plunger.

In some embodiments, frictional coupling may also prevent the plunger from rotating within the base to create a seal when the plunger engages in the second slide position. In other embodiments, the base can be configured to receive the plunger in the second slide position when the bottom surface of the plunger comes into contact with the stop channel. The plunger comprises a radius that is equal to the radius of the receiving channel, forming a frictional fit and a seal.

Figure 8:
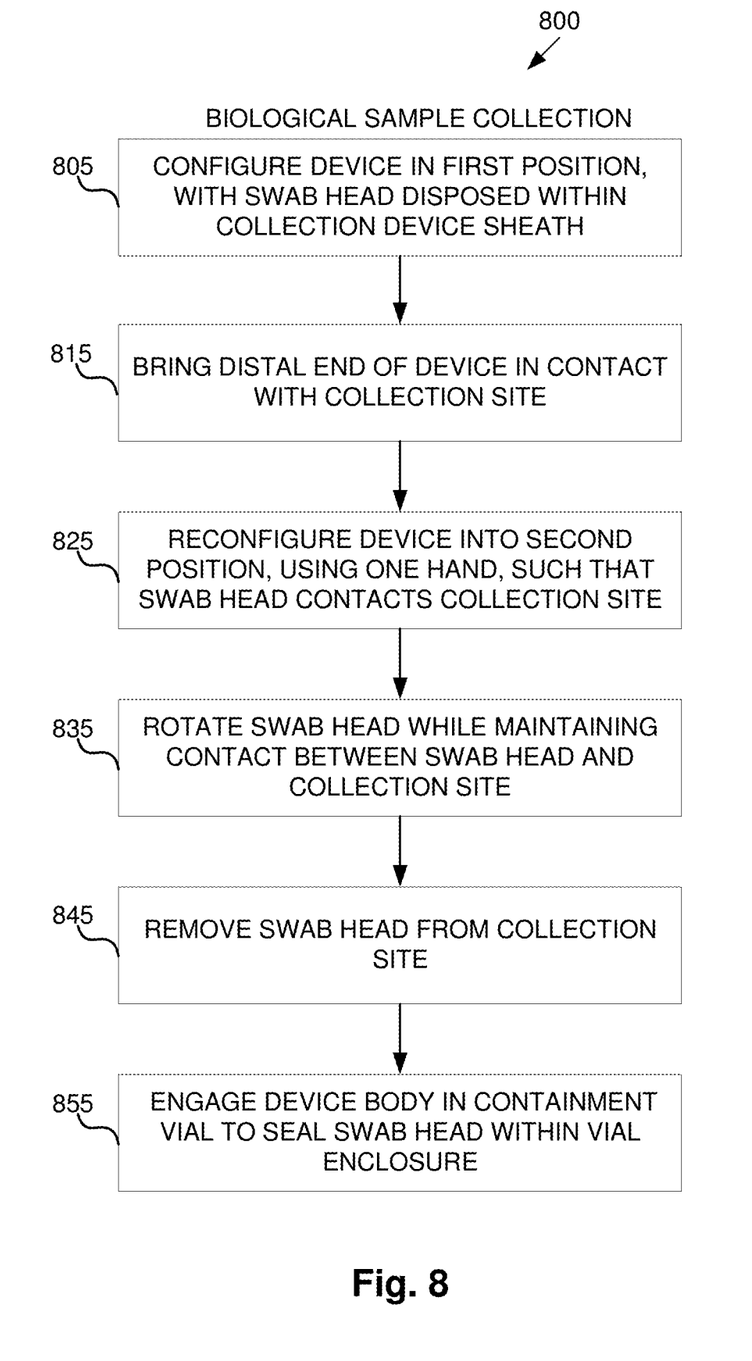
FIG. 8 is a flow chart illustrating a method for collecting a biological sample using a cell collection, storage, and transport device consistent with some embodiments of this disclosure.

FIG. 8 is a flow chart illustrating a method for collecting a biological sample using a cell collection, storage, and transport device. Referring to FIG. 8, biological sample collection process 800 includes configuring a cell collection, storage, and transport device in a first position, with a swab head disposed within the sheath of the collection device at step 805, and bringing the distal end of the device in contact with a collection site at step 815. For example, the collection site may be located along the anal opening or anal canal, in the case where the cells being collected are being used in an anal pap smear, or other related procedure. In some embodiments, the collection site may be located along the vaginal walls, in the case where the cells being collected are being used in a standard pap smear. In other embodiments, the collection site may be located within a wound or along a suspected infection area, in the case where the cells being collected are being used for bacteria culture and detection, or other pathology procedure. In other examples, the cell collection site may be on the surface of the skin or inside the mouth, in cases where the cells being collected are being used for DNA analysis. Other collection sites are possible as would be known in the art, and as would be useful for various biological sample collection purposes. The collection sites may be located on humans or other animal species. The examples of collection sites provided are for exemplary purposes only and are not meant to be limiting.

Still referring to FIG. 8, biological sample collection process 800 may also include reconfiguring the cell collection, storage, and transport device into a second position at step 825, with the swab head extended through an opening at the distal end of the sheath so that it comes in contact with the collection site, and the plunger disposed within the base, as per the exemplary device embodiments illustrated in FIGS. 1, 2, 4A, 4B, and 5. For example, force may be applied to the plunger to cause the shaft and swab head to move through the opening at the distal end of the sheath. In some embodiments, a user may support the sheath in one hand, and using the thumb of that same hand, apply force to the proximal end of the plunger to cause the plunger-shaft-swab head assembly so slide through the distal opening of the sheath.

In some embodiments, biological sample collection process 800 may also include rotating the swab head while maintaining contact between the swab head and the collection site at step 835, as to cause the transfer of the biological sample (e.g., cells) from the collection site and onto the swab head. For example, the swab head may be rotated by applying rotational force, or twisting, the base while the plunger is disposed within the base. For example, in embodiments wherein the plunger frictionally couples to the base, frictional resistance will cause the entire plunger-shaft-swab head assembly to rotate together with the base when rotational force is applied to the base. Accordingly, frictional coupling enables the operation of the cell collection, storage, and transport device by a single user, while holding the device in one hand, such that the biological sample collection procedure may be self-administered. In some embodiments, rotating the swab head at step 835 may include rotating the swab head multiple times (e.g., five times) in one direction (e.g., clockwise), and then rotating the swab head multiple times (e.g., five times) in the opposite direction (e.g., counter-clockwise).

In some embodiments, biological sample collection process 800 may include removing the swab head from the collection site at step 845. The process may also include engaging a collection assembly of the cell collection, storage, and transport device (i.e., the device body) in a containment vial to seal the swab head within the vial enclosure at step 855, consistent with FIGS. 3A and 3B. In some embodiments, the vial enclosure has a flat bottom (distal end) such that the vial may be place on a flat surface while the biological sample collection is taking place, and then the cell collection, storage, and transport device body may be disposed within the vial while the vial still rests on the flat surface. For example, using this collection method, the vial may be pre-filled with a storage fluid as described above, enabling the biological sample collection to take place without spilling the storage fluid.

Figure 9:
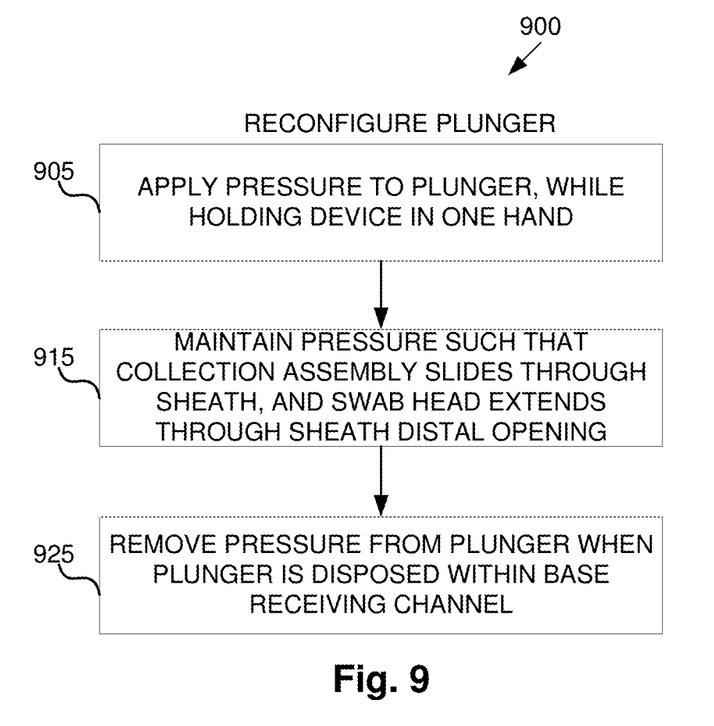
FIG. 9 is a flow chart illustrating a method for reconfiguring a cell collection, storage, and transport device from a first position to a second position, consistent with some embodiments of this disclosure.

FIG. 9 is a flow chart illustrating a method for reconfiguring a cell collection, storage, and transport device from a first position to a second position. Referring to FIG. 9, a process for reconfiguring the plunger of the cell collection, storage, and transport device may include applying pressure to the plunger while holding the cell collection, storage, and transport device in one hand at step 905. The process may further include maintaining pressure on the plunger such that the collection assembly slides through the sheath and the swab head extends through a distal opening of the sheath at step 915. The process may further include removing pressure from the plunger when the plunger is disposed within the base receiving channel at step 925. Step 925 may further include applying sufficient pressure to force the plunger into the receiving channel such that the plunger frictionally couples to the base while disposed within the receiving channel.

Figure 10:
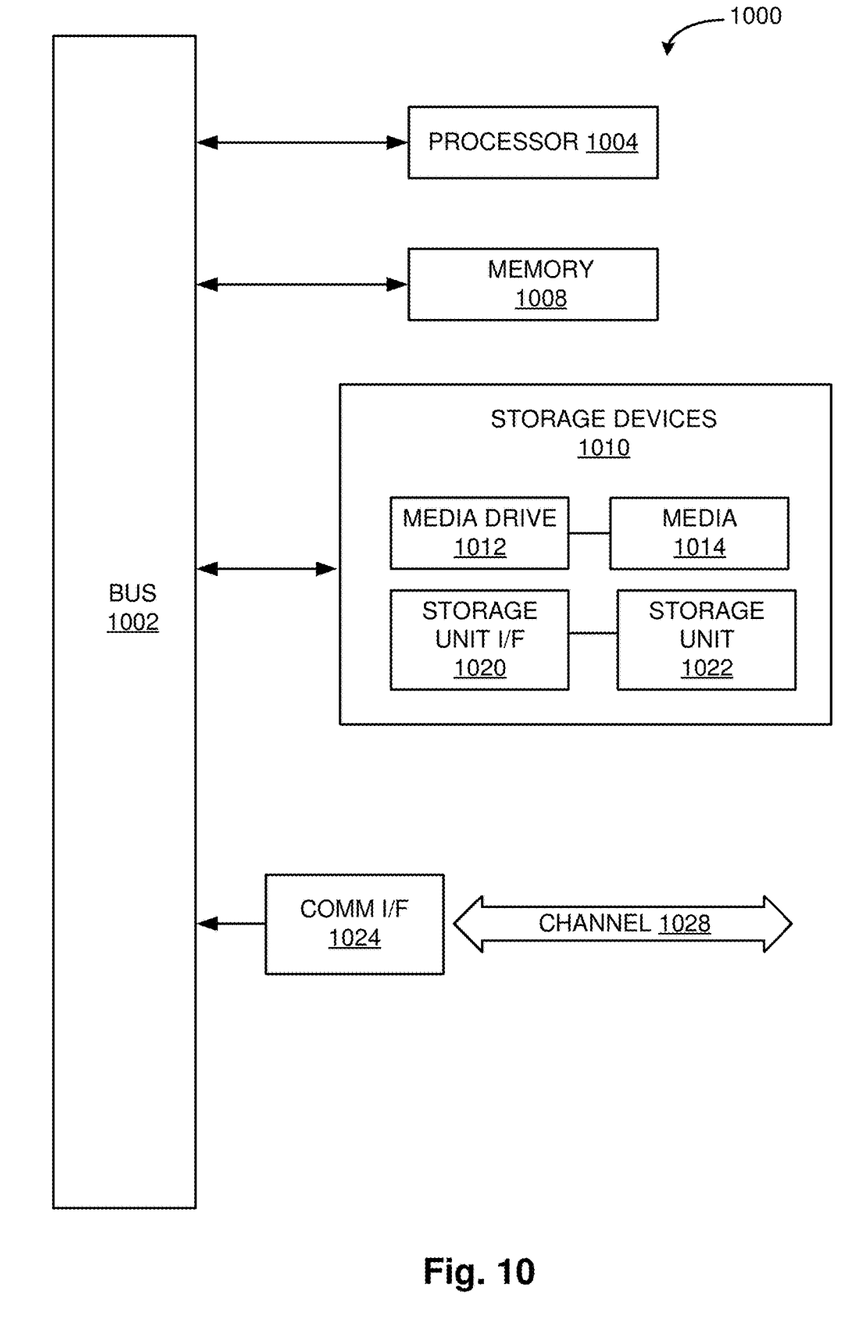
FIG. 10 is a flow chart illustrating a method for reconfiguring a cell collection, storage, and transport device from a first position to a second position, consistent with some embodiments of this disclosure.

As used herein, the term component might describe a given unit of functionality that can be performed in accordance with one or more embodiments of the technology disclosed herein. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. In implementation, the various components described herein might be implemented as discrete components or the functions and features described can be shared in part or in total among one or more components. In other words, as would be apparent to one of ordinary skill in the art after reading this description, the various features and functionality described herein may be implemented in any given application and can be implemented in one or more separate or shared components in various combinations and permutations. As used herein, the term engine may describe a collection of components configured to perform one or more specific tasks. Even though various features or elements of functionality may be individually described or claimed as separate components or engines, one of ordinary skill in the art will understand that these features and functionality can be shared among one or more common software and hardware elements, and such description shall not require or imply that separate hardware or software components are used to implement such features or functionality.

Where servers, mobile devices, engines, components, or components of the technology are implemented in whole or in part using software, in one embodiment, these software elements can be implemented to operate with a computing or processing component capable of carrying out the functionality described with respect thereto. One such example computing component is shown in FIG. 10. Various embodiments are described in terms of this example-computing component 1000. After reading this description, it will become apparent to a person skilled in the relevant art how to implement the technology using other computing components or architectures.

Referring now to FIG. 10, computing component 1000 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing component 1000 might also represent computing capabilities embedded within or otherwise available to a given device. For example, a computing component might be found in other electronic devices such as, for example, digital cameras, navigation systems, cellular telephones, portable computing devices, modems, routers, WAPs, terminals and other electronic devices that might include some form of processing capability.

Computing component 1000 might include, for example, one or more processors, controllers, control components, or other processing devices, such as a processor 804. Processor 804 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing component 1000 or to communicate externally.

Computing component 1000 might also include one or more memory components, simply referred to herein as main memory 1008. For example, preferably random access memory (RAM) or other dynamic memory, might be used for storing information and instructions to be executed by processor 1004. Main memory 1008 might also be used for storing temporary variables or other intermediate information during execution of instructions to be executed by processor 1004. Computing component 1000 might likewise include a read only memory ("ROM") or other static storage device coupled to bus 1002 for storing static information and instructions for processor 1004.

The computing component 1000 might also include one or more various forms of information storage device 1010, which might include, for example, a media drive 1012 and a storage unit interface 1020. The media drive 1012 might include a drive or other mechanism to support fixed or removable storage media 1014. For example, a hard disk drive, a floppy disk drive, a magnetic tape drive, an optical disk drive, a CD or DVD drive (R or RW), or other removable or fixed media drive might be provided. Accordingly, storage media 1014 might include, for example, a hard disk, a floppy disk, magnetic tape, cartridge, optical disk, a CD or DVD, or other fixed or removable medium that is read by, written to or accessed by media drive 1012. As these examples illustrate, the storage media 1014 can include a computer usable storage medium having stored therein computer software or data.

In alternative embodiments, information storage mechanism 1010 might include other similar instrumentalities for allowing computer programs or other instructions or data to be loaded into computing component 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory component) and memory slot, a PCMCIA slot and card, and other fixed or removable storage units 1022 and interfaces 1020 that allow software and data to be transferred from the storage unit 1022 to computing component 1000.

Computing component 1000 might also include a communications interface 1024. Communications interface 1024 might be used to allow software and data to be transferred between computing component 1000 and external devices. Examples of communications interface 1024 might include a modem or softmodem, a network interface (such as an Ethernet, network interface card, WiMedia, IEEE 802.XX, or other interface), a communications port (such as for example, a USB port, IR port, RS232 port, Bluetooth® interface, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium," "computer readable media," and "computer usable medium" are used to generally refer to media such as, for example, memory 1008, storage unit 1020, media 1014, and channel 1028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 1000 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A system for biological sample collection comprising:
    a collection assembly and a sheath;
    wherein the collection assembly comprises a support shaft, a swab head, and a handle;
    the swab head couples to a distal support shaft end;
    the handle comprises a top surface and a bottom surface and couples to a proximal support shaft end;
    a base coupled to a sheath proximal end, the base comprising a stop channel;
    the collection assembly slideably couples to the sheath and is configurable in a retracted position with the swab head entirely disposed within the sheath and the handle extends proximally from the base or an extended position with the swab head extending outside of the sheath, and the handle is disposed within the stop channel such that a radially outward facing handle surface contacts and frictionally couples to a radially inward facing stop channel surface with sufficient force to prevent the handle from rotating when the collection assembly is in the extended position and the swab head is rotated while contacting a collection site;
    a distal sheath end comprises an aperture, the aperture having a circumference large enough to allow the swab head to pass through said aperture when the collection assembly is configured in the extended position; and
    a seal configured to be applied to the distal sheath end after the swab head has collected a biological sample and the collection assembly has been reconfigured into the retracted position.

2. The system of claim 1, wherein the sheath is configured to fit into a palm of a hand and the handle comprises a ring configured to fit around a finger or thumb from the hand to enable one-handed operation of the collection assembly into the retracted position or the extended position.

3. The system of claim 1, wherein the handle is larger than a circumferential profile of a proximal sheath end and the handle contacts the proximal sheath end when the collection assembly is in the extended position, as to prevent the collection assembly from being over-extended.

4. The system of claim 1, wherein the seal comprises an adhesive backing to enable the seal to adhere to the distal sheath end.

5. The system of claim 1, wherein the seal comprises a cap configured to sealably couple to the distal sheath end.

6. The system of claim 1, wherein the seal comprises a plastic film.

7. The system of claim 1, wherein the sheath comprises an identification label located on an outside surface, the identification label comprising identification information for a collected sample.

8. A method for biological sample collection comprising:
    identifying a collection site;
    providing a collection device comprising:
        a sheath and a collection assembly slideably coupled to the sheath, the collection assembly comprising a support shaft, a swab coupled to a distal support shaft end, a handle coupled to a proximal support shaft end, the handle comprising a top surface and a bottom surface;
        a base coupled to a sheath proximal end, the base comprising a stop channel;

configuring the collection device in a first position, such that the swab head is completely disposed within the sheath and the handle extends proximally from the base;

moving a distal sheath end close to the collection site; and configuring the sample collection device into a second position by applying pressure to the handle, such that the swab head fully extends through a proximal opening in the sheath, and the handle is disposed within the stop channel such that a radially outward facing handle surface contacts and frictionally couples to a radially inward facing stop channel surface with sufficient force to prevent the handle from rotating when the collection assembly is in the extended position and the swab head is rotated while contacting the collection site;

applying the swab head to the collection site to collect a biological sample;

configuring the collection assembly into the first position; and attaching a seal over the distal sheath end to enclose the swab head and the biological sample.

9. The method of claim 8, wherein the seal comprises a plastic film with an adhesive backing configured to adhere to the distal sheath end.

10. The method of claim 8, wherein the seal comprises a cap configured to mechanically couple to the distal sheath end.

11. The method of claim 8, wherein the collection site is a nasal cavity or an oral cavity.

12. The method of claim 8, further comprising operating the collection device with a single hand.

* * * * *